United States Patent
Kather et al.

(10) Patent No.: US 9,629,646 B2
(45) Date of Patent: Apr. 25, 2017

(54) CURVED BURR SURGICAL INSTRUMENT

(71) Applicants: IMDS Corporation, Logan, UT (US); Jens Kather, Benglen (CH); Michael Schueler, Kreuszlingen (CH)

(72) Inventors: Jens Kather, Benglen (CH); Joshua A. Butters, Chandler, AZ (US); Jeffery D. Arnett, Gilbert, AZ (US); Dylan M. Hushka, Gilbert, AZ (US); Nicholas M. Slater, Chandler, AZ (US); Bradford J. Coale, Flanders, NJ (US)

(73) Assignees: Jens Kather, Benglen (CH); Michael Schueler, Kreuzlingen (CH); IMDS Corporation, Providence, UT (US)

( * ) Notice: Subject to any disclaimer, the term of this patent is extended or adjusted under 35 U.S.C. 154(b) by 210 days.

(21) Appl. No.: 13/763,084

(22) Filed: Feb. 8, 2013

(65) Prior Publication Data
US 2014/0018834 A1  Jan. 16, 2014

Related U.S. Application Data

(60) Provisional application No. 61/670,540, filed on Jul. 11, 2012.

(51) Int. Cl.
*A61B 17/32* (2006.01)
*A61B 17/16* (2006.01)

(52) U.S. Cl.
CPC ........ *A61B 17/32* (2013.01); *A61B 17/32002* (2013.01); *A61B 17/1659* (2013.01); *A61B 17/1664* (2013.01)

(58) Field of Classification Search
CPC . A61B 17/16; A61B 17/1604; A61B 17/1613; A61B 17/1615; A61B 17/1617; A61B 17/162; A61B 17/1622; A61B 17/1633; A61B 17/1637; A61B 17/164; A61B 17/1642; A61B 17/1659; A61B 17/1662; A61B 17/1664; A61B 17/1666; A61B 17/1668; A61B 17/1675; A61B 17/1677; A61B 17/1684; A61B 17/17; A61B 17/1735; A61B 17/32; A61B 17/320016; A61B 17/32002; A61B 2017/1602; A61B 2017/320004; A61B 2017/320008; A61B 2017/320012; A61B 2017/320024; A61B 2017/320028;
(Continued)

(56) References Cited

U.S. PATENT DOCUMENTS 1,314,601 A  9/1919  McCaskey
1,630,239 A  5/1927  Brinkley
(Continued)

FOREIGN PATENT DOCUMENTS

CN  213482 Y  6/1993
CN  201055399  5/2008
(Continued)

*Primary Examiner* — Kevin T Truong
*Assistant Examiner* — Tracy Kamikawa
(74) *Attorney, Agent, or Firm* — Dienwiebel Transatlantic IP (57) ABSTRACT

A tissue resection device may include an hourglass shaped burr to resect tissue according to the shape and curvature of the hourglass shaped burr. The tissue resection device may also include a depth stop window and a movable protective guard to control the amount of cutting.

13 Claims, 9 Drawing Sheets

(58) Field of Classification Search
CPC ......... A61B 2017/320032; A61B 2017/32004; A61B 2017/320056
USPC ....... 606/79, 80, 83–85, 167, 170–172, 180; 83/633, 613, 618, 617, 124, 141; 30/113.1, 113.3, 114, 123.5
See application file for complete search history.

(56) References Cited

U.S. PATENT DOCUMENTS

| | | | |
|---|---|---|---|
| 1,677,337 A | 7/1928 | Grove | |
| RE29,736 E | 8/1978 | Shea | |
| 4,264,307 A | 4/1981 | Neuwirth | |
| 4,285,618 A | 8/1981 | Shanley | |
| 4,445,509 A | 5/1984 | Auth | |
| 4,541,423 A | 9/1985 | Barber | |
| 4,646,738 A | 3/1987 | Trott | |
| 4,751,922 A | 6/1988 | Dipietropolo | |
| 4,842,578 A | 6/1989 | Johnson | |
| 4,950,277 A | 8/1990 | Farr | |
| 4,984,581 A | 1/1991 | Stice | |
| 4,990,134 A | 2/1991 | Auth | |
| 5,047,040 A | 9/1991 | Simpson | |
| 5,067,489 A | 11/1991 | Lind | |
| 5,069,569 A | 12/1991 | Lieser | |
| 5,147,364 A | 9/1992 | Comparetto | |
| 5,226,909 A | 7/1993 | Evands | |
| 5,322,505 A | 6/1994 | Krause | |
| 5,360,432 A | 11/1994 | Shturman | |
| 5,387,218 A | 2/1995 | Meswania | |
| 5,411,514 A | 5/1995 | Fucci | |
| 5,468,243 A | 11/1995 | Halpern | |
| 5,488,761 A | 2/1996 | Leone | |
| 5,527,316 A | 6/1996 | Stone | |
| 5,554,163 A | 9/1996 | Shturman | |
| 5,556,408 A | 9/1996 | Farhat | |
| 5,569,277 A * | 10/1996 | Evans et al. ................ | 606/159 |
| 5,569,284 A | 10/1996 | Young | |
| 5,584,843 A | 12/1996 | Wulfman | |
| 5,620,447 A | 4/1997 | Smith | |
| 5,759,185 A | 6/1998 | Grinberg | |
| 5,810,827 A * | 9/1998 | Haines .................. | A61B 17/155 606/80 |
| 5,851,208 A | 12/1998 | Trott | |
| 5,904,681 A | 5/1999 | West, Jr. | |
| 5,908,423 A | 6/1999 | Kashuba | |
| 5,913,867 A | 6/1999 | Dion | |
| 6,027,460 A | 2/2000 | Shturman | |
| 6,053,907 A | 4/2000 | Zirps | |
| 6,053,922 A | 4/2000 | Krause | |
| 6,053,923 A | 4/2000 | Veca | |
| 6,068,641 A | 5/2000 | Varsseveld | |
| 6,126,667 A | 10/2000 | Barry | |
| 6,197,064 B1 | 3/2001 | Haines | |
| 6,214,009 B1 | 4/2001 | Toriumi | |
| 6,217,595 B1 | 4/2001 | Shturman | |
| 6,235,042 B1 | 5/2001 | Katzman | |
| 6,299,623 B1 | 10/2001 | Wulfman | |
| 6,312,438 B1 | 11/2001 | Adams | |
| 6,358,251 B1 | 3/2002 | Mirza | |
| 6,423,078 B1 | 7/2002 | Bays | |
| 6,482,209 B1 | 11/2002 | Engh | |
| 6,638,288 B1 | 10/2003 | Shturman | |
| 6,645,218 B1 | 11/2003 | Cassidy | |
| 6,656,195 B2 | 12/2003 | Peters | |
| 6,740,090 B1 | 5/2004 | Cragg | |
| 6,949,101 B2 | 9/2005 | McCleary | |
| 7,115,131 B2 | 10/2006 | Engh | |
| 7,118,574 B2 | 10/2006 | Patel | |
| 7,393,355 B2 | 7/2008 | Tulkis | |
| 7,507,245 B2 | 3/2009 | Shturman | |
| 7,520,901 B2 | 4/2009 | Engh | |
| 7,555,343 B2 | 6/2009 | Bleich | |
| 7,559,928 B2 | 7/2009 | Johnson | |
| 7,585,300 B2 * | 9/2009 | Cha .................. | 606/80 |
| 7,604,637 B2 | 10/2009 | Johnson | |
| 7,637,910 B2 | 12/2009 | Schmieding | |
| 7,682,378 B2 | 3/2010 | Truckai | |
| 7,717,932 B2 | 5/2010 | McFarlin | |
| 7,785,337 B2 | 8/2010 | Adams | |
| 7,896,880 B2 | 3/2011 | Bonutti | |
| 7,918,796 B2 | 4/2011 | Nyca | |
| 7,922,720 B2 | 4/2011 | May | |
| 7,935,117 B2 | 5/2011 | Sackett | |
| 7,985,225 B2 | 7/2011 | Johnson | |
| 8,006,578 B2 | 8/2011 | Kiester | |
| 8,070,762 B2 | 12/2011 | Escudero | |
| 8,114,083 B2 | 2/2012 | Haines | |
| 8,123,750 B2 | 2/2012 | Norton | |
| 8,137,277 B2 | 3/2012 | Nycz | |
| 8,157,766 B2 | 4/2012 | Bonnette | |
| 8,157,825 B2 | 4/2012 | Shturman | |
| 8,172,846 B2 | 5/2012 | Brunnett | |
| 8,473,305 B2 | 6/2013 | Belcher | |
| 2001/0034526 A1 | 10/2001 | Kuslich | |
| 2003/0055404 A1 | 3/2003 | Moutafis | |
| 2004/0098006 A1 | 5/2004 | Nakanishi | |
| 2004/0147934 A1 | 7/2004 | Kiester | |
| 2005/0113836 A1 | 5/2005 | Lozier | |
| 2005/0197661 A1 | 9/2005 | Carrison | |
| 2005/0203508 A1 | 9/2005 | Thelen | |
| 2005/0203527 A1 | 9/2005 | Carrison | |
| 2005/0209610 A1 | 9/2005 | Carrison | |
| 2005/0234477 A1 | 10/2005 | Brown | |
| 2006/0142775 A1 | 6/2006 | Heneberry | |
| 2006/0149268 A1 | 7/2006 | Truckai | |
| 2006/0178594 A1 | 8/2006 | Neubardt | |
| 2006/0217751 A1 | 9/2006 | O'Quinn | |
| 2007/0060933 A1 * | 3/2007 | Sankaran ............... | A61B 17/16 606/160 |
| 2007/0118135 A1 | 5/2007 | Mansmann | |
| 2007/0197895 A1 | 8/2007 | Nycz | |
| 2007/0260256 A1 | 11/2007 | Beaule | |
| 2008/0208230 A1 | 8/2008 | Chin | |
| 2009/0048602 A1 | 2/2009 | O'Donoghue | |
| 2009/0270894 A1 | 10/2009 | Rubin | |
| 2009/0326538 A1 | 12/2009 | Sennett | |
| 2010/0036403 A1 | 2/2010 | O'Quinn | |
| 2010/0121365 A1 | 5/2010 | O'Sullivan | |
| 2010/0145343 A1 | 6/2010 | Johnson | |
| 2010/0152738 A1 | 6/2010 | Holko | |
| 2010/0179557 A1 | 7/2010 | Husted | |
| 2010/0229688 A1 | 9/2010 | Adams | |
| 2010/0266984 A1 | 10/2010 | Jung | |
| 2010/0280624 A1 | 11/2010 | Ench | |
| 2010/0286694 A1 | 11/2010 | Rio | |
| 2010/0286698 A1 | 11/2010 | Del Rio | |
| 2010/0298832 A1 | 11/2010 | Lau | |
| 2011/0004215 A1 | 1/2011 | Bradley | |
| 2011/0015639 A1 | 1/2011 | Metzger | |
| 2011/0015749 A1 | 1/2011 | Engh | |
| 2011/0034930 A1 | 2/2011 | Buschmann | |
| 2011/0125160 A1 | 5/2011 | Bagga | |
| 2011/0196399 A1 * | 8/2011 | Robertson et al. ........... | 606/169 |
| 2011/0238099 A1 | 9/2011 | Loreth | |
| 2011/0270258 A1 | 11/2011 | Johnson | |
| 2011/0270293 A1 | 11/2011 | Malla | |
| 2011/0319896 A1 | 12/2011 | Papenfuss | |
| 2012/0004662 A1 | 1/2012 | Torrie | |
| 2012/0046526 A1 | 2/2012 | Boettner | |
| 2012/0083788 A1 | 4/2012 | Blakemore | |
| 2012/0116405 A1 | 5/2012 | Long | |
| 2012/0116532 A1 | 5/2012 | Forsell | |
| 2012/0150209 A1 | 6/2012 | Gubellini | |
| 2012/0209273 A1 | 8/2012 | Zaretzka | |
| 2012/0221007 A1 | 8/2012 | Batten | |
| 2013/0023882 A1 | 1/2013 | Fabro | |

FOREIGN PATENT DOCUMENTS

| | | |
|---|---|---|
| CN | 101433468 | 5/2009 |
| DE | 3840466 | 6/1990 |
| DE | 102004046539 | 5/2012 |
| EP | 1389458 | 2/2004 |
| EP | 1787593 | 5/2007 |

(56) References Cited

FOREIGN PATENT DOCUMENTS

| EP | 2426456 | 10/2010 |
|----|---------|---------|
| GB | 2220729 | 1/1990 |
| GB | 2426455 | 11/2006 |
| UA | 20384 | 1/2007 |
| WO | WO 9215255 | 9/1992 |
| WO | WO 2004075719 | 9/2004 |
| WO | WO 2004110251 | 12/2004 |
| WO | WO 2007003243 | 1/2007 |
| WO | WO 2010033473 | 3/2010 |
| WO | WO 2011023410 | 3/2011 |
| WO | WO 2011060077 | 5/2011 |
| WO | WO 2012004766 | 1/2012 |

\* cited by examiner

CURVED BURR SURGICAL INSTRUMENT

CROSS-REFERENCE TO RELATED APPLICATIONS

This application claims the benefit of the following:

U.S. Provisional Patent Application No. 61/670,540, filed Jul. 11, 2012, entitled CURVED BURR SURGICAL INSTRUMENT.

The above-referenced document is hereby incorporated by reference in its entirety.

BACKGROUND

The present disclosure relates to surgical instrumentation. While the present disclosure is made in the context of femoroacetabular impingement (FAI) surgery of the hip, it is understood that the principles herein may be applicable in other tissue removal applications, whether arthroscopic, laparoscopic, endoscopic, or open, including but not limited to: foot, knee, hip, pelvis, spine, ribs, shoulder, elbow, wrist, hand, craniomaxillofacial, etc.

Straight, rigid tissue cutting instruments are not well suited to creating a smooth anatomic radius of curvature with minimal manipulation. With these tools, it is up to the surgeon to attempt to sculpt a three-dimensional (3D) anatomic surface by precisely manipulating the cutter over the treated surface, without accidentally removing too much tissue. This requires great skill, practice, patience and time.

It is desirable to provide a more efficient means of tissue removal, including removal of sclerotic bone, in order to reduce operating time. The disclosed examples are capable of removing tissue on multiple curved surfaces at once, creating a smooth uniform surface with minimal manipulation of the cutting tip. The instruments described herein may automatically re-establish a proper anatomic curvature to the treated surface by matching the natural anatomic curvature of the tissue. The instruments described herein are capable of producing 3D shaping with simple two-dimensional (2D) manipulation of the instruments. The instruments and methods described herein may significantly reduce operating time and produce more uniform results.

In one embodiment of the present technology, the tissue resection device includes a hollow member with a window formed therein, a drive member, and a rotary cutting member having a concave or hourglass shape that is at least partially exposed from the outer housing. The hourglass shaped cutting element may be curved to approximately match the geometry of the tissue to be resected. The device may also be fitted with a protective hood, or sheath with at least one cutout or window through which the cutting element or burr may be exposed. The window may be sized and shaped to vary the amount of burr exposure through the window to control the amount and/or depth of tissue that is removed in a single pass of the instrument. In this manner, the size and shape of the window may act as a "depth stop" to provide extra control and precision over tissue removal and prevent accidental or excessive tissue removal. The depth stop window may be sized and shaped to achieve a substantially uniform cut depth along the curved burr portion of the resection device. The window in the outer sheath may be sized and shaped to allow the burr to project a predetermined amount from the window to limit the amount of tissue removed in a single pass. Moreover, the window in the outer sheath may be sized and shaped to track the curvature of the burr such that the burr projects uniformly from the window along the length of the curved burr to achieve a substantially uniform depth cut at each point along the length of the curved burr. The protective hood may also be rotatable or translatable to selectively cover all or a portion of the burr. The protective hood and/or hollow member may be made of transparent material.

In some embodiments, the user may selectively adjust how much the burr projects from the window. In this manner, the user may control the depth of the tissue cut in a single pass to allow for quick tissue resection or for slower, more "finely-tuned", tissue resection.

BRIEF DESCRIPTION OF THE DRAWINGS

While exemplary embodiments of the present technology have been shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

In the following Detailed Description, various features are grouped together in several embodiments for the purpose of streamlining the disclosure. This method of disclosure is not to be interpreted as reflecting an intention that exemplary embodiments of the technology require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear. Similar reference numbers (e.g., those that are identical except for the first numeral) are used to indicate similar features in different embodiments.

DETAILED DESCRIPTION

Standard medical planes of reference and descriptive terminology are employed in this specification. A sagittal plane divides a body into right and left portions. A midsagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body.

In this specification, standard hip anatomical terms are used with their customary meanings.

The following disclosure is made in the context of femoroacetabular impingement (FAI) surgery of the hip for the purposes of illustration. The principles of the disclosed technology are applicable to a variety of other tools and instruments beyond the scope of FAI.

Figure 1:
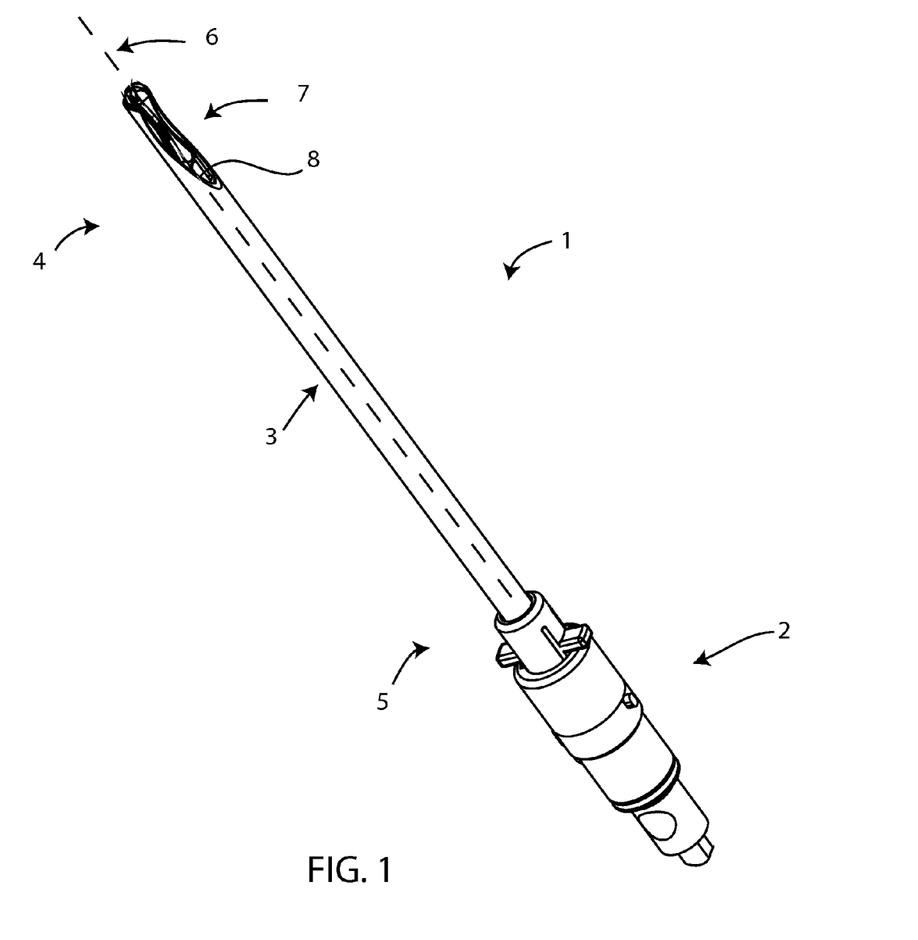
FIG. 1 is an isometric view of a tissue resection device.

Referring to FIG. 1, a tissue resection device 1 may include a drive adapter hub 2, a hollow member 3, and a rotary cutting member 7. The hollow member 3 has a proximal end 5, a distal end 4, and a central axis 6. The drive adapter hub 2 is coupled to the hollow member 3 at the proximal end 5. The rotary cutting member 7 is disposed at the distal end 4 of the hollow member 3. The rotary cutting member 7 may be described as a burr. The tissue resection device 1 may also incorporate a suction port 8 to aid in removing tissue debris. In some examples, the drive adapter hub 2 may be adapted for grasping the tissue resection device and manipulating the position of the tissue resection device in any direction or orientation. For example, the drive adapter hub 2 may be adapted to interact with a powered hand piece (not shown) forming a handle for grasping the tissue resection device and manipulating the position of the tissue resection device in any direction or orientation. In other examples, the drive adapter hub 2 may include an integral handle formed thereon. In still other examples, the drive adapter hub 2 may be externally textured or may have a high friction outer surface for grasping.

Figure 2:
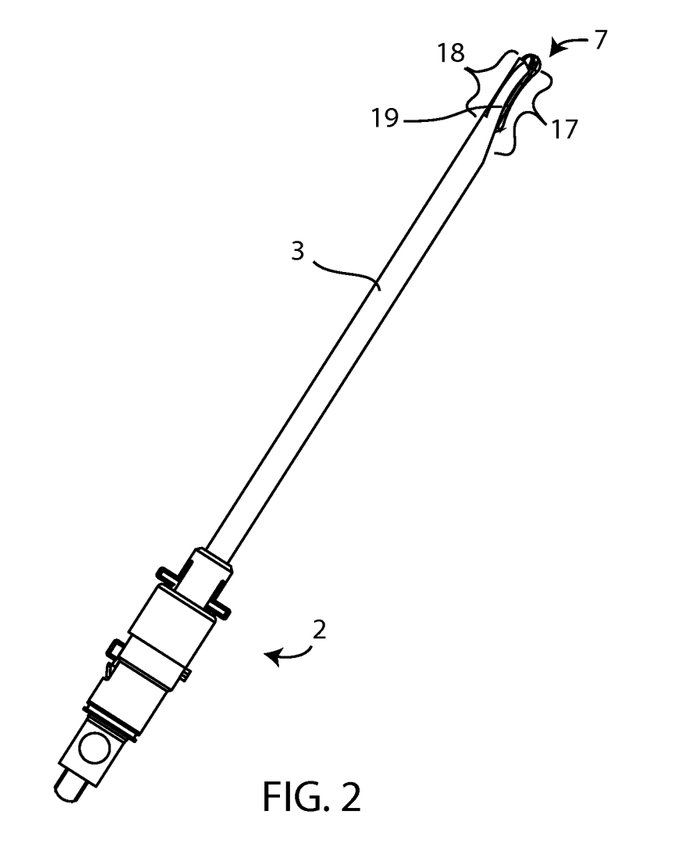
FIG. 2 is a side view of the tissue resection device of FIG. 1.

FIG. 2 shows the tissue resection device 1 from a side view. The hollow member 3 may have an opening or window 17 formed in the distal end 4 of the hollow member 3. The opening or window 17 may be formed along the axis 6 of the hollow member 3 and sized and shaped to allow the rotary cutting member 7 to be partially exposed and protrude from the window 17. The shape of the window 17 in the direction of the axis 6 of the hollow member 3 may have edges 19 that are concave shaped and substantially similar to the concave shape of the rotary cutting member 7. The rotary cutting member 7 may protrude uniformly past the edges 19. The concave shaped edges 19 of the window 17 may thus act as depth stops to limit the amount of tissue that is resected during a single pass of the tissue resection device 1. In one example, the rotary cutting member 7 protrudes about 1.5 mm past the concave shaped edges 19 of the window 17. In other examples, the rotary cutting member 7 protrudes less than 1.5 mm beyond the concave shaped edges 19 of the window 17. In still other examples, the rotary cutting member 7 protrudes more than 1.5 mm beyond the concave shaped edges 19 of the window 17. In some examples, the user may selectively adjust the amount that the rotary cutting member 7 protrudes from the concave shaped edges 19 of the window 17.

The concave shaped edges 19 may also give the user better control by contacting the tissue during resection on one or both sides of the rotary cutting member 7. The edges 19 may provide stability to the resection device 1 by resisting twisting forces caused by the rotary cutting member as it spins and resects tissue. The edges 19 may also provide stability to the resection device by providing a multi-contact stabilizing reference to help the user keep the burr or rotary cutting member 7 in the desired position, similar to a tripod or a tool rest. For example, there may be a first contact point or area between the burr 7 and the tissue as the burr 7 resects the tissue; a second contact point or area between the tissue and a first concave shaped edge 19, and a third contact point or area between the tissue and a second concave shaped edge 19 opposite the first concave shaped edge. Each additional contact point provides greater stability and control to the user.

A distal top portion 18 of the hollow member 3 may be entirely or partially formed of transparent material to allow the user to see the rotary cutting member 7 during use. In some examples, the rotary cutting member 7 may be fully exposed with no distal top portion 18 or protective hood 21 (discussed below) adjacent the rotary cutting member 7, or any window 17 with concave shaped edges 19 to act as depth stops.

Figure 3:
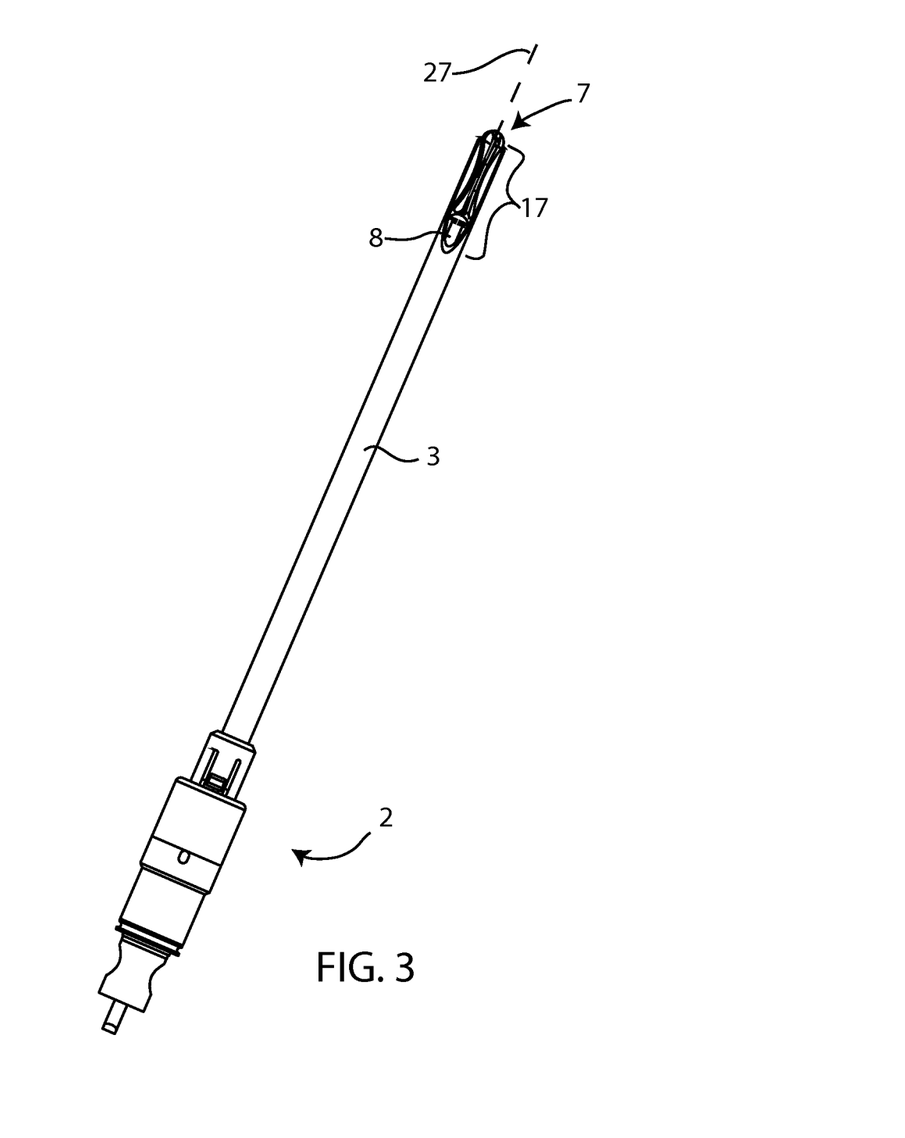
FIG. 3 is a bottom view of the tissue resection device of FIG. 1.

FIG. 3 shows a bottom view of the tissue resection device 1 illustrating the window 17 formed in the hollow member 3 and the concave or hourglass shaped rotary cutting member 7 exposed through the window 17. The rotary cutting member 7 may have an elongated body 9 that lies along an elongate body central longitudinal axis 27. In some examples, the rotary cutting member 7 may be coaxial with the axis 6 of the hollow member 3. In other examples, the axis 27 may be parallel to the axis 6.

Figure 4:
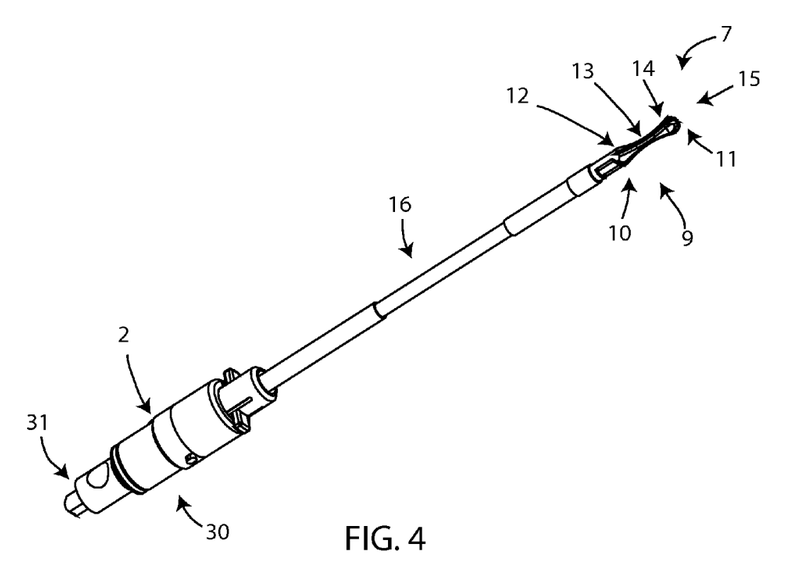
FIG. 4 is an isometric view of the tissue resection device of FIG. 1 with a hollow member removed.

FIG. 4 shows the tissue resection device 1 with the hollow member 3 removed to expose a drive member 16. The drive member 16 may transmit rotational forces, or torque, from the hub 2. The hub 2 may transmit torque from a powered hand piece (not shown), which may be connected to a suitable power source (not shown). The hub 2 may include a drive feature 31, for example a triangular, rectangular, square, or hexagonal shaft, for complementary interconnection with the powered hand piece.

The rotary cutting member 7 may have one or more cutting features on the elongate body 9. FIG. 4 shows an example with cutting flutes along the length of the elongate body 9 of the rotary cutting member 7. The cutting flutes may be of any size, shape, or number. The cutting flutes may be axial as shown, or they may be helical clockwise or counterclockwise. The cutting flutes may cross to produce a diamond pattern of cutting projections. The rotary cutting member 7 may have a first portion 12, a second portion 14, a third or middle portion 13, and a fourth portion 15. The rotary cutting member 7 may have a concave or hourglass shape between the proximal end 10 and the distal end 11 of the rotary cutting member 7. The first portion 12 may have a first width or diameter, the second portion 14 may have a second width or diameter, and the middle portion 13 may have a third width or diameter. The first width of the first portion 12 and the second width of the second portion 14 may be greater than the third width of the middle portion 13 to form a concave curve between the first portion 12 and the second portion 14 of the rotary cutting member 7. The first, second, and third widths or diameters may be measured over the cutting features, and may thus correspond to the dimensions cut by the rotary cutting member 7. The concave shape of the rotary cutting member 7 may be chosen to substantially correspond to the natural or desired curvature of the tissue to be resected. For example, the concave shape of the rotary cutting member 7 may be chosen to substantially correspond to the natural curvature of the femoral neck of a human bone. In other examples, the concave shape of the rotary cutting member 7 may be chosen to substantially correspond to the natural or desired curvature of any tissue including, but not limited to, any bone, cartilage, soft tissue, and the like.

Continuing with FIG. 4, rotary cutting member 7 may have a fourth portion or end cutter 15 formed on the distal end 11 of the elongate body 9 of the rotary cutting member 7. In some examples, the end cutter portion 15 is at least partially hemispherical in shape. In other examples, the end cutter portion 15 may be substantially flat, conical, dished, or another shape. The end cutter portion 15 may have flutes, cutting members, or abrasive material formed thereon and configured to resect tissue. For example, the end cutter portion 15 may be useful in removing pincer-type bone impingements on an acetabular rim during femoral acetabular impingement (FAI) surgery. In other examples, the rotary cutting member 7 may terminate in a smooth non-cutting end portion instead of an end cutter.

FIGS. 5-9 illustrate another tissue resection device 40 that is similar to device 1, but includes an outer sheath 20 having a protective hood 21 and a protective hood window 23 formed on the distal end of the outer sheath 20. In this example, the outer sheath 20 is a tubular structure that fits over a hollow member 3. The protective hood window 23 may be similar to window 17. The window 23 may be formed along the axis 6 of the hollow member 3 and sized and shaped to allow the rotary cutting member 7 to be partially exposed and protrude from the protective hood window 23 formed in the hollow member 3. The shape of the protective hood window 23 in the direction of the axis 6 of the hollow member 3 may have edges 24 that are concave and substantially similar to the concave shape of the rotary cutting member 7. The concave shaped edges 24 of the protective hood window 23 may thus act as depth stops to limit the amount of tissue that is resected during a single pass of the tissue resection device 40. The protective hood may be made of transparent material to help the user visualize the placement and action of the rotary cutting member 7. In one example, the outer sheath 20 may be rotated by manipulating the control member 25 located at a proximal end of the outer sheath 20. For example, a user may apply compressive and/or rotational forces to tabs 26 of the control member 25 to rotate the outer sheath 20 about the hollow member 3 and control the position of the protective hood 21 relative to the rotary cutting member 7. In this manner, the protective hood 21 may be selectively positioned to expose the rotary cutting member 7 to allow tissue to be resected, or positioned to cover the rotary cutting member 7 to prevent tissue from being resected, or positioned to partially cover the rotary cutting member 7.

Figure 5:
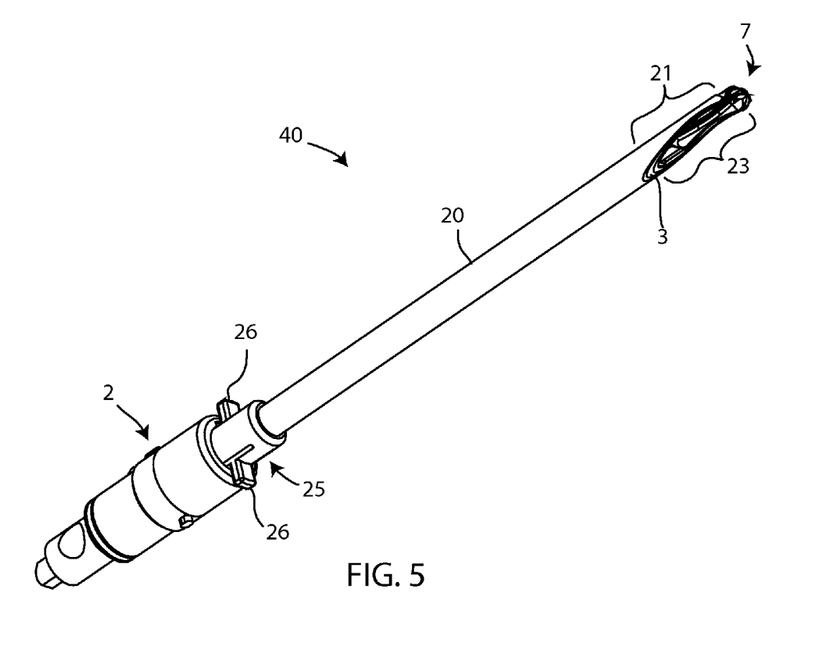
FIG. 5 is an isometric view of another tissue resection device which incorporates an outer sheath with a protective hood.
Figure 6:
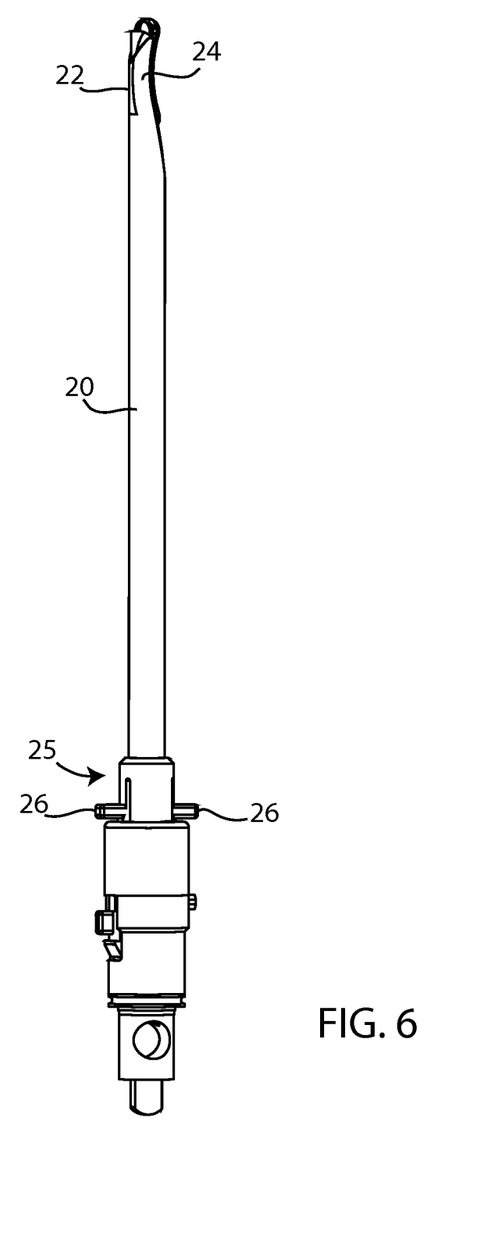
FIG. 6 is a side view of the tissue resection device of FIG. 5 with the protective hood positioned in a first position.
Figure 7:
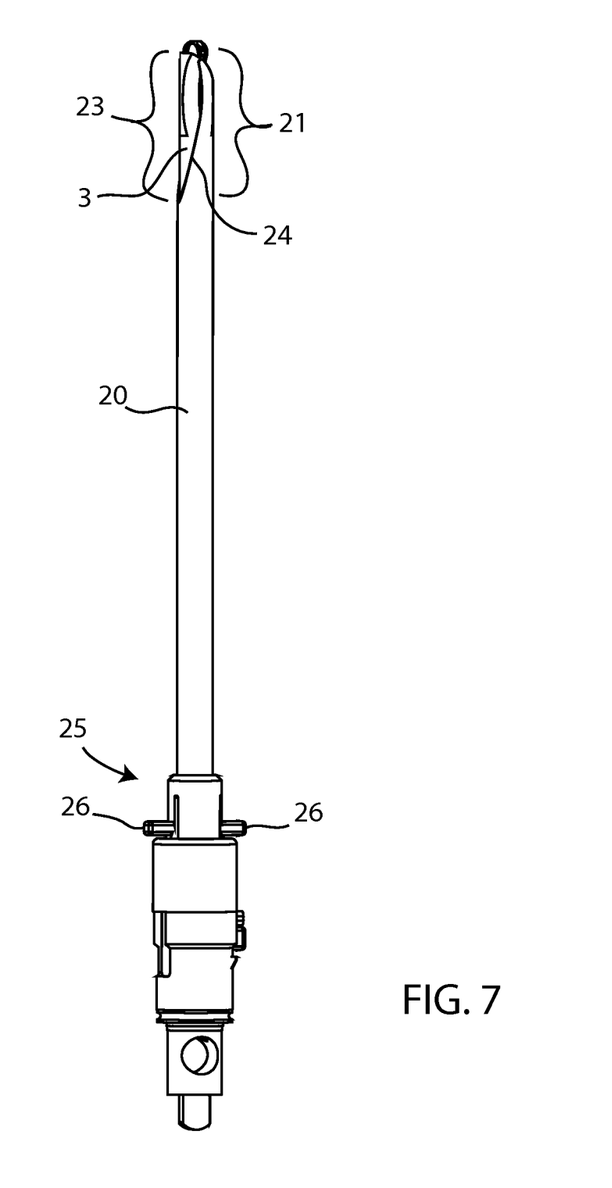
FIG. 7 is a side view of the tissue resection device of FIG. 5 with the protective hood positioned in a second position.
Figure 8:
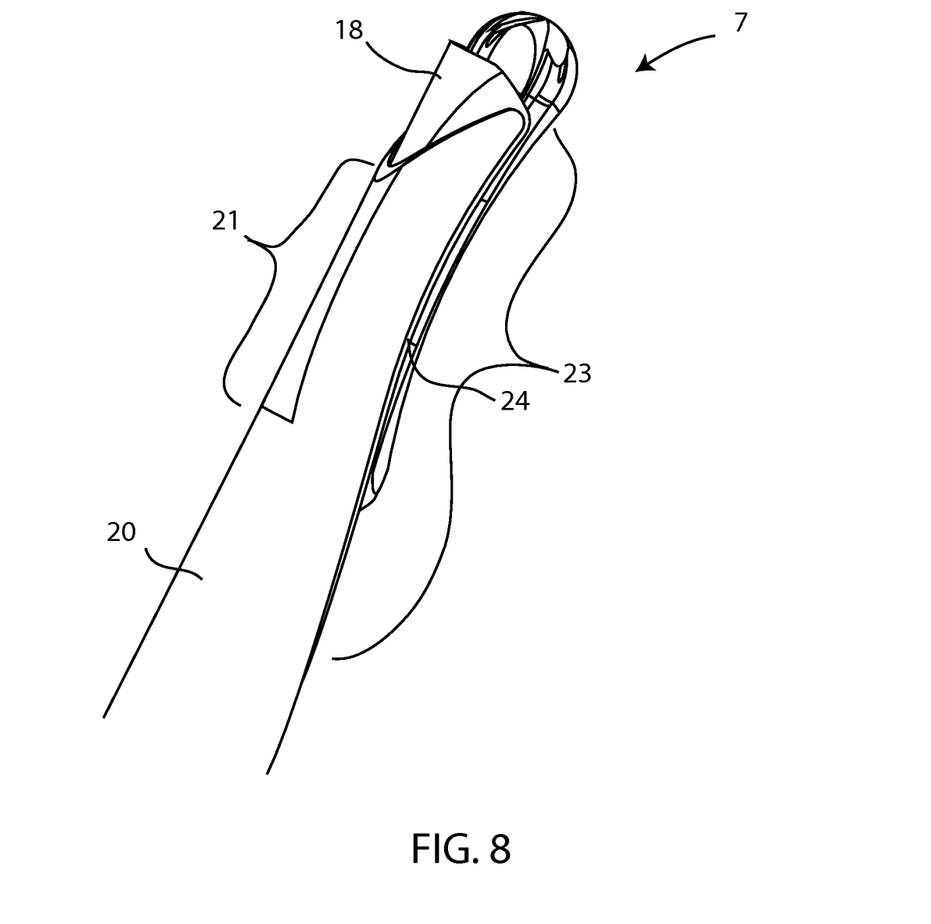
FIG. 8 is a close-up side view of the tissue resection device of FIG. 6 with the protective hood in the first position.
Figure 9:
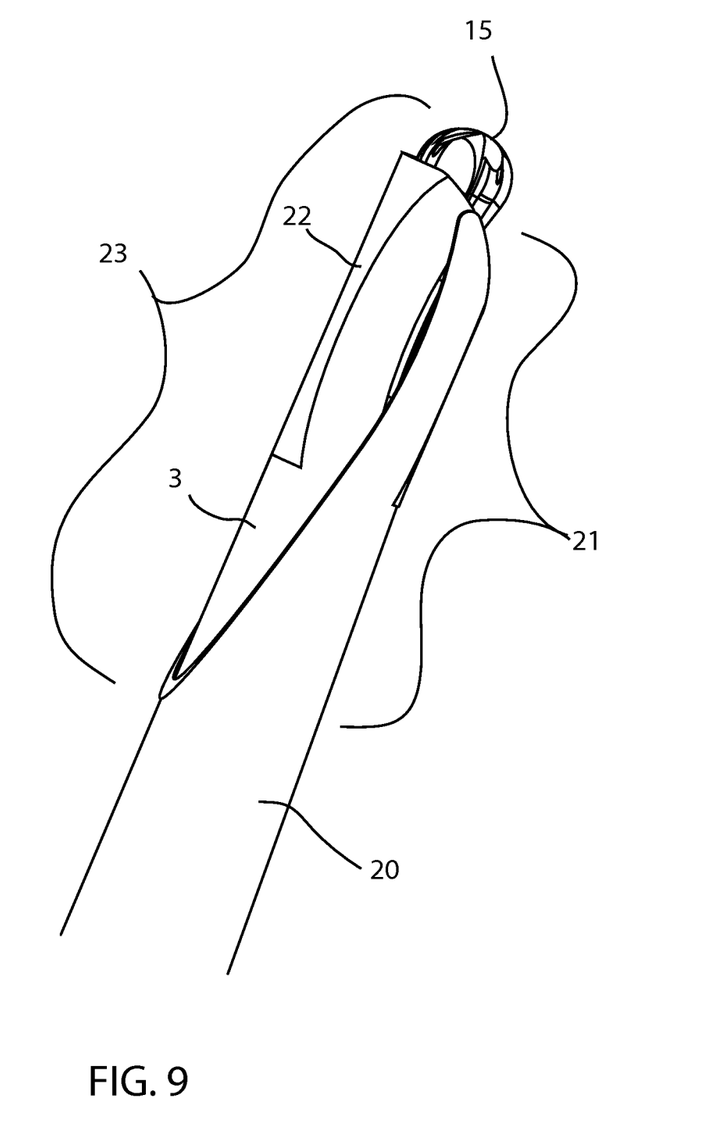
FIG. 9 is a close-up side view of this tissue resection device of FIG. 7 with the protective hood in the second position.

FIGS. 5, 6, and 8 show the tissue resection device 40 with the outer sheath 20 rotationally oriented such that the protective hood window 23 of the outer sheath 20 is aligned with the window 17 of the hollow member 3. This allows the rotary cutting member to be exposed through both windows 23, 27 and enables the rotary cutting member 7 to resect tissue. FIGS. 7 and 9 show the tissue resection device 40 with the outer sheath 20 rotationally oriented such that the protective hood window 23 of the outer sheath 20 faces the window 17 of the hollow member 3. This covers up the rotary cutting member 7 and prevents the rotary cutting member 7 from resecting tissue along the curved portion of the rotary cutting member 7. In some examples, the end-cutting portion 15 of the rotary cutting member 7 always remains exposed at the distal tip of the tissue resection device 40 regardless of the rotational orientation of the outer sheath 20. In other examples, the end-cutting portion 15 of the rotary cutting member 7 may be selectively covered or uncovered to allow or prevent the end-cutting portion 15 from resecting tissue. In one such example, the outer sheath 20 and the hollow member 3 may extend distally to cover some of the end-cutting portion 15. When the protective hood window 23 of the outer sheath 20 is aligned with the window 17 of the hollow member 3, some of the end-cutting portion 15 is exposed. When the protective hood window 23 of the outer sheath 20 faces the window 17 of the hollow member 3, the end-cutting portion 15 is covered up. In another such example, the outer sheath may be translatable along the axis 6 of the hollow member 3 to cover portions of the rotary cutting member 7. For example, the outer sheath 20 may be translated in the distal direction to substantially cover up all or a portion of the hourglass and/or end cutting portions 15 of the tissue resection device 40. Thus, it will be understood, that the outer sheath 20 may be both rotatably and axially positionable.

It is to be understood that a rotatable or translatable protective hood 21 may be used with any surgical instrument, besides burrs, to cover up the end effector disposed at the distal end of the hollow member 3. Example end effectors include, but are not limited to: grasping jaws, dissectors, suture passers, staplers, tissue cutters, rasps, ablation devices, microfracture devices, scalpels, shavers, cameras, sensors, etc., or any other end effector or structure.

With reference to FIG. 8, it may be seen that when the outer sheath 20 is rotated to the open position, the rotary cutting member 7 and the suction port are exposed through the window 23 and the suction created by suction port 8 is proximal to the rotary cutting member 7. Thus, suction power is positioned close to the curved portion of the rotary cutting member 7 where it is needed to remove tissue debris. In contrast, when the outer sheath 20 is rotated to the closed position, the protective hood 21 covers the curved portion of the rotary cutting member 7 and the suction port 8. This directs suction distally toward the end-cutting portion 15 of the rotary cutting member 7, as may be seen in FIG. 9. Thus, the design of the outer sheath 20 automatically shifts fluid suction between the proximal part of the rotary cutting member 7 to the distal end-cutting portion 15 of the rotary cutting member 7 as the outer sheath 20 is rotated.

Similarly, in other examples, the outer sheath 20 may be axially translatable to automatically direct fluid suction forces between the proximal part of the rotary cutting member 7 and the distal end-cutting portion 15 of the rotary cutting member as the outer sheath 20 translates back and forth in the axial direction.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Different materials may be used within a single part. Any component disclosed herein may be colored, coded or otherwise marked to make it easier for a user to identify the type and size of the component, the setting, the function(s) of the component, and the like.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A tissue resection device, comprising:
   a hollow member having a proximal end, a distal end, and a longitudinal axis;
   a drive member situated at least partly within the hollow member;
   a rotary cutting member for side cutting, the rotary cutting member having an elongate body with a longitudinal axis, a proximal end, and a distal end, wherein the proximal end of the elongate body is coupled to the drive member and wherein the elongate body has an hourglass shaped section between the proximal end of the elongate body and the distal end of the elongate body along the longitudinal axis of the elongate body;
   the hollow member comprising an opening, formed in the distal end of the hollow member along the longitudinal axis of the hollow member, the opening of the hollow member sized and shaped to partially expose the rotary cutting member through the opening of the hollow member, the shape of the opening in the direction of the axis of the hollow member having edges that are concave shaped and are substantially similar to the hourglass shaped section of the elongate body, wherein the rotary cutting member partially protrudes from the opening of the hollow member;
   and a protective hood adapted to partially surround the rotary cutting member, wherein the protective hood comprises a second opening formed in a distal end of the protective hood along the longitudinal axis of the elongate body, the second opening of the protective hood being sized and shaped to partially expose the rotary cutting member through the second opening of the protective hood, wherein the shape of the second opening of the protective hood in the direction of the longitudinal axis of the elongate body has edges that are concave shaped and are substantially similar to the hourglass shaped section of the elongate body.

2. The tissue resection device of claim 1, wherein the rotary cutting member is coaxial with and received within the hollow member.

3. The tissue resection device of claim 1, wherein the longitudinal axis of the rotary cutting member is parallel to or identical with the longitudinal axis of the hollow member, wherein the rotary cutting member is received within the hollow member.

4. The tissue resection device of claim 1, wherein a distance that the rotary cutting member protrudes from the opening of the hollow member is selectively adjustable.

5. The tissue resection device of claim 1, wherein the elongate body of the rotary cutting member further comprises an end cutting portion formed in the distal end of the elongate body of the rotary cutting member.

6. The tissue resection device of claim 5, wherein the end cutting portion is at least partially hemispherical in shape.

7. The tissue resection device of claim 1, wherein the protective hood is rotatable about the longitudinal axis of the elongate body to selectively cover and uncover the rotary cutting member.

8. The tissue resection device of claim 1, wherein at least a portion of the hollow member surrounding the rotary cutting member comprises a transparent material.

9. The tissue resection device of claim 1, wherein the rotary cutting member comprises: a first portion having a first width; a second portion having a second width; and a middle portion having a third width, the middle portion intermediate the first portion and the second portion, wherein the first width of the first portion and the second width of the second portion are greater than the third width of the middle portion.

10. The tissue resection device of claim 1, wherein the protective hood can be selectively translated along the longitudinal axis of the hollow member to cover or uncover the rotary cutting member.

11. The tissue resection device of claim 1, wherein the opening provides a depth stop.

12. The tissue resection device of claim 1, wherein the rotary cutting member is a burr.

13. The tissue resection device of claim 1, wherein the rotary cutting member is a rasp.

* * * * *